US00PP20117P2

(12) United States Plant Patent
Bradford

(10) Patent No.: US PP20,117 P2
(45) Date of Patent: Jun. 23, 2009

(54) PEACH TREE NAMED 'NEPTUNE V'

(50) Latin Name: *Prunus persica*
Varietal Denomination: Neptune V

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 12/080,829

(22) Filed: Apr. 7, 2008

(51) Int. Cl.
*A01H 5/00* (2006.01)

(52) U.S. Cl. ..... Plt./198

(58) Field of Classification Search ..... Plt./198
See application file for complete search history.

(56) References Cited

PUBLICATIONS

U.S. Appl. No. 11/453,792 by Bradford.

*Primary Examiner*—Susan B McCormick Ewoldt

(57) ABSTRACT

The present invention relates to a new and distinct variety of peach tree, *Prunus persica,* broadly characterized by a medium size, vigorous, hardy, self-fertile, productive and regular bearing tree. The variety blooms during the mid season and requires about 625 chilling hours. The fruit matures under the ecological conditions described in mid June, with first picking on Jun. 16, 2007. The fruit is uniformly medium in size, sub-acidic and sweet in flavor, very oblate in shape, freestone in type, firm and melting in texture, yellow in flesh color, and mostly red in skin color.

1 Drawing Sheet

Botanical classification: *Prunus persica.*
Variety denomination: 'Neptune V'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of peach tree, which has been denominated varietally as 'Neptune V'.

The present variety was hybridized by me in 2000 as a first generation cross using 'Grand Pearl' (U.S. Plant Pat. No. 9,960) nectarine as the selected seed parent and 'Neptune I' (U.S. Plant Pat. No. 18,816) peach as the selected pollen parent. The fruit of this cross was gathered that summer, and the seeds were removed, cracked, stratified, germinated, and grown as seedlings on their own root in my greenhouse. Upon reaching dormancy the seedlings were transplanted as a group to a cultivated area of my experimental orchard located near Le Grand, Calif., in Merced County (San Joaquin Valley). During the fruit evaluation season of 2004 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent 'Grand Pearl' nectarine by producing fruit that is mostly red in skin color and sweet and sub-acidic in taste, but is quite distinguished therefrom by being a peach instead of a nectarine, and by producing fruit that is yellow flesh instead of white, that is freestone instead of clingstone, and that matures about twenty-five days earlier.

The present variety is more similar to its pollen parent, 'Neptune I' (U.S. Plant patent application Ser. No. 11/453,792) peach by producing peaches that are very oblate in shape, firm, freestone in type, and mostly red in skin color, but is distinguished therefrom by producing fruit that is sweeter in flavor, that is yellow instead of white in flesh color, and that matures about twenty-five days earlier.

SUMMARY OF VARIETY

In summary, the present variety is characterized by a medium size, vigorous, hardy, self-fertile, productive and regular bearing tree. The variety blooms during the mid season and requires about 625 chilling hours. The fruit matures under the ecological conditions described in mid June, with first picking on Jun. 16, 2007. The fruit is uniformly medium in size, sub-acidic and sweet in flavor, very oblate in shape, freestone in type, firm and melting in texture, yellow in flesh color, and mostly red in skin color.

DRAWING

The accompanying photograph consists of four whole fruits positioned to display the characteristics of the skin color and form, two half fruits to reveal the flesh and stone, typical leaves, and a tip shoot.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jun. 19, 2007, on the original tree during its seventh growing season. The blossom and flower descriptions were made the previous blooming season. All major color code designations are by reference to the Inter-Society Color Council, National Bureau of Standards. Common color names are also used occasionally.

Parentage

Seed parent: 'Grand Pearl' (U.S. Plant Pat. No. 9,960) nectarine.

Pollen parent: 'Neptune I' (U.S. Plant Pat. No. 18,816) peach.

Tree

Size: Medium, reaching and maintaining a height of 10' [3.05 m.] and a spread of 6' [1.83 m.] after seven growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Approximate chilling requirement: 625 hours.

Trunk:

*Size.*—Slender, reaching a maximum diameter of 2½" [64 mm.] after the seventh growing season.

*Texture.*—Shaggy.

*Bark color.*—A Grayish yellowish brown [80. gy.yBr] and Brownish gray [64. brGy] variegation.

*Lenticels.*—Approximate Number Per Square Inch: 7. Color: Dark orange yellow [72. d.OY]. Average Size: ¼" [6.4 mm.]. Shape: Eye-shaped, elongated.

Branches:

*Size.*—Diameter of limb is 1½" [38.1 mm.] measured 12" above the crotch, 1¼" [31.8 mm.] measured 12" above the first fork.

*Texture.*—Smooth on first and second year wood, increasing roughness with age.

*Color.*—1st Year Wood Topside: Grayish red [19. gy.R]. 1st Year Wood Underside: Brilliant yellow green [116. brill.YG]. Second Year Wood: A Grayish brown [61. gy.Br] and Moderate brown [58. m.Br] variegation.

*Lenticels.*—Number Per Square Inch: More than 30 on second year wood. Color: Strong yellowish brown [74. s.yBr]. Average size: 1/32" [0.8 mm.] on second year wood. Shape: Rectangular, elongated.

Leaves:

*Size.*—Medium. Average Length: 5½" [140 mm.]. Average Width: 1⅝" [41 mm.].

*Arrangement.*—Alternate.

*Thickness.*—Medium.

*Form.*—Elliptical.

*Apex.*—Acuminate.

*Base.*—Acute, with an average base angle of 70 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Pale yellow green [121. p.YG].

*Petiole.*—Average Length: ⅜" [9.5 mm.]. Average Thickness: 1/16" [1.6 mm.]. Color: Strong yellow green [117. s.YG].

*Stipules.*—Number: Usually 2 per leaf, up to 6 per growing tip. Average Length: ¼" [6.4 mm.]. Color: Brilliant yellow green [116. brill.YG] becoming Moderate reddish brown [43. m.rBr] with maturity.

*Glands.*—Number: 2 to 4 per leaf. Position: Alternately positioned on petiole and base of blade. Size: Large. Form: Reniform. Color: Brilliant yellow green [116. brill.YG] becoming Strong yellowish brown [74. s.yBr] with age.

*Leaf buds.*—Pointed, medium in size.

Flower buds:

*Hardiness.*—Hardy, with respect to central California winters.

*Diameter.*—Typically ⅜" [9.5 mm.] 1 week before bloom.

*Length.*—Typically 11/16" [17.5 mm.] 1 week before bloom.

*Form.*—Not appressed.

*Surface.*—Pubescent.

*Tip color.*—Deep pink [3. deep Pk].

Flowers: Perfect, complete, perigynous, usually a single pistil, typically thirty or more stamens, five sepal and petal locations alternately positioned.

*Type.*—Showy, large.

*Average flower diameter.*—2" [50.8 mm.].

*Number of petals.*—Predominately five, extra petal fragments or are full double blossoms very rare.

*Petal shape.*—Circular to oval.

*Petal margin.*—Entire, wavy, occasional notches.

*Average petal diameter.*—13/16" [20.6 mm.].

*Average petal length.*—⅞" [22.2 mm.].

*Petal apex.*—Rounded.

*Petal base.*—Rounded to somewhat truncate.

*Petal color.*—Pale pink [7. p.Pk] toward the apex, Light pink [4. l.Pk] toward the base on both sides.

*Anther color.*—Strong red [12. s.R] over a Strong orange yellow [68. s.OY] center at bloom onset.

*Stigma color.*—Pale yellow green [121. p.YG].

*Sepal color.*—Deep purplish red [256. deep pR] on the outer surface.

*Sepal length.*—7/32" [5.6 mm.].

*Sepal width.*—7/32" [5.6 mm.].

*Sepal apex.*—Rounded to elliptical to match the sepal length and width.

*Sepal margin.*—Fairly smooth.

*Average pistil length.*—9/16" [14.3 mm.].

*Average stamen length.*—⅝" [15.9 mm.].

*Fragrance.*—Moderate.

*Blooming period.*—Medium, with 'August Red' (U.S. Plant Pat. No. 6,363) nectarine.

*Onset of bloom.*—One percent on Mar. 2, 2007.

*Date of full bloom.*—Mar. 9, 2007.

*Duration of bloom.*—One to two weeks, dependent on ambient temperature.

*Number per cluster.*—1 to 3 with single flowers most common.

FRUIT

Maturity when described: Firm ripe, Jun. 19, 2007.
Date of first picking: Jun. 16, 2007.
Date of last picking: Jun. 24, 2007.
Size: Uniform, medium.
*Average diameter axially.*—1⅜" [34.9 mm.].
*Average diameter across suture plane.*—2⅞" [73.0 mm.].
*Average diameter across cheek plane.*—2 15/16" [74.6 mm.].
*Typical weight.*—5.1 ounces [145 grams].
Form: Uniform, slightly asymmetrical, strongly compressed axially.
*Longitudinal section form.*—Toroidal, very oblate.
*Axial view.*—Elliptical with suture protrusions.
Suture: Extends from the base, along the side, and beyond the pistil point.
*Near the base.*—A shallow, sharp groove.
*Along the side.*—A distinct trough.
*Near the apex.*—A shallow groove.
Ventral surface: Rounded, lipped throughout.
Lips: Unequal.
Cavity: Flaring, very elongated in the suture plane, suture showing on both sides, Light yellow [86. l.Y] stem markings typical.
*Depth.*—¼" [6.4 mm.].
*Breadth.*—1¼" [31.8 mm.].
Base: Truncate.
Apex: Truncate, but very cordate if viewed parallel to the suture.
Pistil point: Apical, neglible in length, depressed within the suture.
Stem: Medium.
*Average length.*—¼" [6.4 mm.].
*Average width.*—3/16" [4.8 mm.].
Skin:
*Thickness.*—Medium.
*Surface.*—Smooth.
*Tenacity.*—Tenacious to flesh.
*Astringency.*—Non-astringent.
*Tendency to crack.*—Very slight.
*Color.*—Dark red [16. d.R] smoothly blending into a Strong reddish orange [35. s.rO] background.
*Down.*—Scant, does not roll up when rubbed.
Flesh:
*Color.*—Very yellow [82. v.Y] with minor Moderate red [15. m.R] streaking toward the stone full maturity.
*Surface of pit cavity.*—Covered with Moderate pink [5. m.Pk] fibers.
*Amygdalin.*—Scarce.
*Juice.*—Moderate, rich.
*Texture.*—Firm, melting.
*Fibers.*—Abundant, fine, tender.
*Ripens.*—Earlier toward the apex.
*Flavor.*—Mildly sub-acidic, typically 16 to 18 brix.
*Aroma.*—Slight.
*Eating quality.*—Very good.

STONE

Type: Freestone.
Form: Elliptical.
Hilum: Narrow, oblong.
Base: Rounded.
Apex: Rounded with a 1/16" [1.6 mm.] tip.
Sides: Equal.
Surface: Furrowed on both sides of the dorsal fin, pitted throughout.
External color: Light yellowish brown [76. l.yBr].
Pit wall color when cracked: Moderate yellowish brown [77. m.yBr].
Cavity surface color: Light grayish yellowish brown [79. l.gy.yBr].
Average pit wall thickness: ⅛" [3.2 mm.].
Average width: ⅞" [22.2 mm.].
Average length: 9/16" [14.3 mm.].
Average breadth: 15/16" [23.8 mm.].
Tendency to split: Very slight.
Kernel:
*Form.*—Oval.
*Skin color.*—Light yellow [86. l.Y] when first removed.
*Pellicle color.*—Strong yellowish brown [74. s.yBr].
*Vein color.*—Pale yellow [89. p.Y].
*Taste.*—Bitter.
*Viable.*—Yes.
*Average width.*—3/16" [4.8 mm.].
*Average length.*—¼" [6.4 mm.].
*Amygdalin.*—Abundant.

Use

Market: Fresh market and long distance shipping.
Keeping quality: Good, fruit quality observed to remain in good condition after 14 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is similar to its pollen parent, 'Neptune I' (U.S. Plant Pat. No. 18,816) peach by producing peaches that are very oblate in shape, firm, freestone in type, and mostly red in skin color, but is distinguished therefrom by producing fruit that is sweeter in flavor, that is yellow instead of white in flesh color, and that matures about twenty-five days earlier.

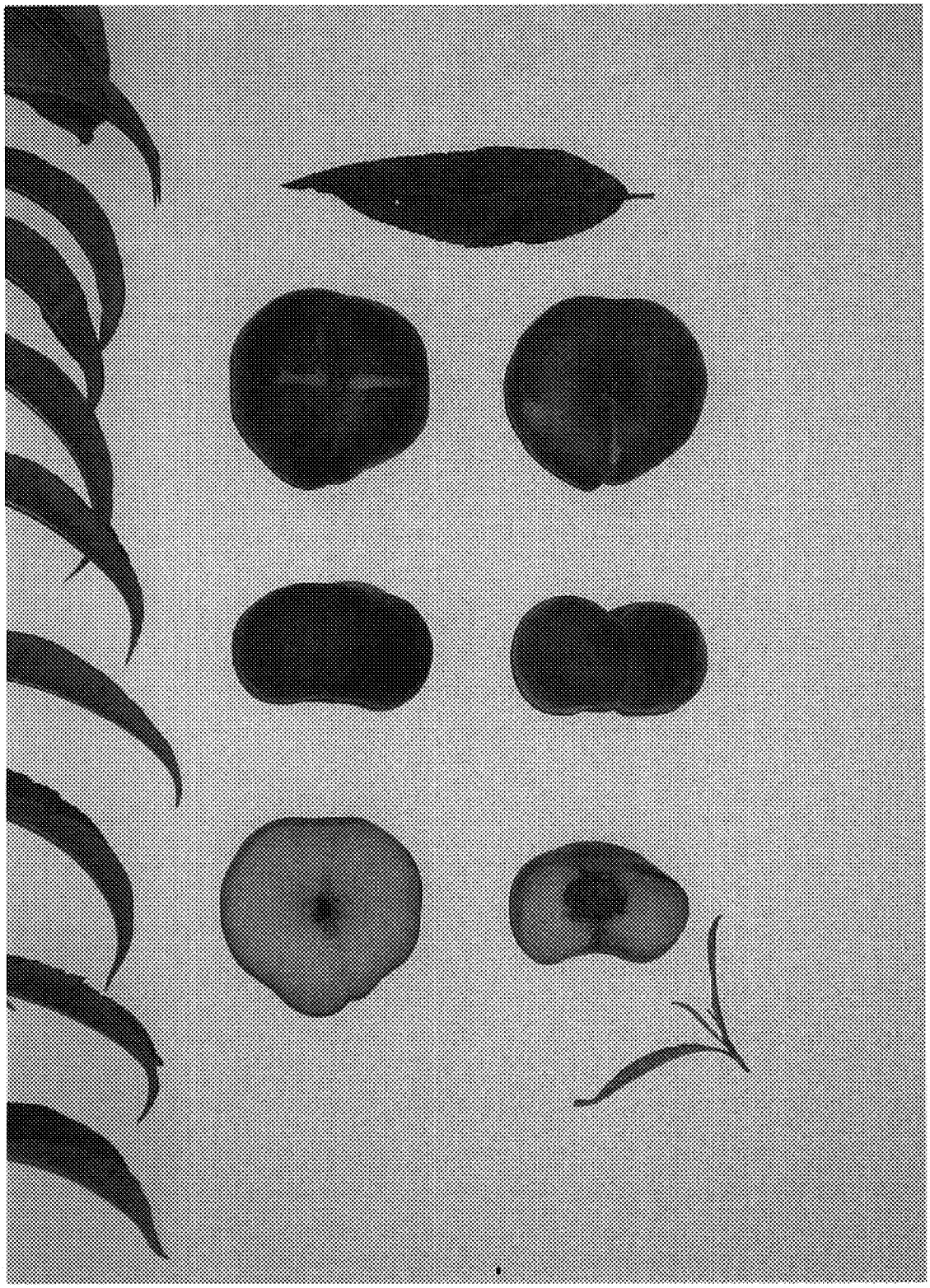

* * * * *